United States Patent [19]

Rinehart

[11] 4,066,440

[45] Jan. 3, 1978

[54] SYMMETRICAL ALKYNYL UREAS

[75] Inventor: Jay K. Rinehart, Akron, Ohio

[73] Assignee: PPG Industries, Inc., Pittsburgh, Pa.

[21] Appl. No.: 701,398

[22] Filed: June 30, 1976

Related U.S. Application Data

[63] Continuation-in-part of Ser. No. 620,984, Oct. 9, 1975, abandoned, which is a continuation of Ser. No. 383,843, July 30, 1973, abandoned.

[51] Int. Cl.$^2$ .............................................. A01N 9/20

[52] U.S. Cl. ................................ 71/119; 260/553 R; 424/322

[58] Field of Search .......................................... 71/119

[56] References Cited

U.S. PATENT DOCUMENTS

| | | | |
|---|---|---|---|
| 2,867,520 | 1/1959 | Beaver et al. | 71/120 |
| 3,126,272 | 3/1964 | Fischer et al. | 71/119 |
| 3,594,362 | 7/1971 | Szabo | 71/119 |
| 3,685,982 | 8/1972 | Weis et al. | 71/119 |

OTHER PUBLICATIONS

Sato, C.A. 53, (1959), 5112f.
Matzner, et al., Chem. Rev., 64, (1964), pp. 656–658.
Winteler, et al., C.A., 49, (1955), 6094f.

*Primary Examiner*—Joseph P. Brust
*Attorney, Agent, or Firm*—Robert J. Grassi

[57] ABSTRACT

Disclosed are symmetrical alkynyl ureas, such as N,N'-bis-(3-methyl-1-butyn-3-yl)urea, their manufacture by the reaction of a chloroformate such as beta-fluoroethyl chloroformate with alkynes such as 3-amino-3-methyl-1-butyne, and their use to control certain weeds, fungi, and bacteria.

7 Claims, No Drawings

SYMMETRICAL ALKYNYL UREAS

CROSS REFERENCE TO RELATED APPLICATIONS

This application is a continuation-in-part of application Ser. No. 620,984, filed Oct. 9, 1975, now abandoned, which is a continuation of application Ser. No. 383,843, filed July 30, 1973, now abandoned.

BACKGROUND OF THE INVENTION

1. Field of the Invention

The invention is to novel chemical compounds of symmetrical alkynyl ureas having an alkynyl of from 3 to 5 carbon atoms, such as the urea, N,N'-bis-(3-methyl-1-butyn-3-yl)urea, to a method of preparing them, and to methods of using them as a pesticide, especially against weeds, fungi, and bacteria.

2. Description of the Prior Art

Herbicidal ureas which contain an aryl or alkyl group in their structure, but not alkynyls like the compounds of this invention, for example those in U.S. Pat. Nos. 3,126,272, 2,867,520, and 3,594,362. Consequently, there appears to be no basis for expecting the symmetrical alkynyl ureas such as N,N'-bis-(3-methyl-1-butyn-3-yl)urea to control certain weeds, fungi, and bacteria.

Moreover, the usual result in organic chemistry when a chloroformate is reacted with an amine is the formation of a corresponding carbamate, rather than the formation of an urea, as shown in Matzner et al, *Chemical Reviews,* Vol. 64, pp. 656–658 (1964) and Winteler et al, *Chemical Abstracts,* Vol. 49, Col. 6094–6095 (1955).

Furthermore, yellow nutsedge (*Cyperus esculentus*), a common weed, is known to resist the action of many of the commonly used chemical herbicides. There is need for novel chemicals that are herbicidally active against yellow nutsedge and others of the genus Cyperus. There is a very great need for chemicals that in addition to being effective against yellow nutsedge are also effective against certain fungi and bacteria.

SUMMARY OF THE INVENTION

The invention concerns novel symmetrical alkynyl ureas of the general formula

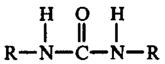

wherein R is an alkynyl of from 3 to 5 carbon atoms, particularly alkynyls of 2-propynyl, 2-butynyl, 3-butynyl, 2-pentynyl, 3-pentynyl, 4-pentynyl, 1-methyl-2-propynyl, 1-ethyl-2-propynyl, and 1,1-dimethyl-2-propynyl, their manufacture by the reaction of the appropriate amino-alkynyl with a beta-fluoroethylchloroformate or a beta-chloroethylchloroformate. The invention also concerns methods of controlling weeds of the genus Cyperus, especially the specie *Cyperus esculentus* (yellow nutsedge), with these ureas especially N,N'-bis-(3-methyl-1-butyn-3-yl)urea, fungi of the genus Sclerotium, and Phytophthora, and bacteria of the genus Xanthomonas, particularly the species *Sclerotium rolfsii, Phytophthora infestans,* and *Xanthomonas vesicatoria* with the ureas, especially with N,N'-bis-(3-methyl-1-butyn-3-yl)urea.

DESCRIPTION OF THE PREFERRED EMBODIMENTS

The symmetrical alkynyl ureas are those of the general graphic formula

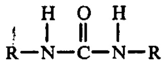

wherein R is an alkynyl of from 3 to 5 carbon atoms. Preferably the alkynyl is 2-propynyl, 2-butynyl, 3-butynyl, 2-pentynyl, 3-pentynyl, 4-pentynyl, 1-methyl-2-propynyl, 1-ethyl-2-propynyl, or 1,1-dimethyl-2-propynyl. Representative examples of the alkynyl ureas of the general formula are:

N,N'-bis-(2-propynyl)urea;
N,N'-bis-(2-butynyl)urea;
N,N'-bis-(3-butynyl)urea;
N,N'-bis-(2-pentynyl)urea;
N,N'-bis-(3-pentynyl)urea;
N,N'-bis-(4-pentynyl)urea;
N,N'-bis-(1-methyl-2-propynyl)urea, also referred to herein and in the claims as N,N'-bis-(3-butyn-2-yl)urea;
N,N'-bis-(1-ethyl-2-propynyl)urea, also referred to as N,N'-bis-(1-pentyn-3-yl)urea;
N,N'-bis-(1,1-dimethyl-2-propynyl)urea, also referred to herein and in the claims as N,N'-bis-(3-methyl-1-butyn-3-yl)urea;
N,N'-bis-(1-methyl-2-butynyl)urea; and
N,N'-bis-(1-methyl-3-butynyl)urea.

Those symmetrical alkynyl ureas are highly preferred which have alkynyls of 2-propynyl, 1-methyl-2-propynyl, and 1,1-dimethyl-2-propynyl. The compound N,N'-bis-(3-methyl-1-butyn-3-yl)urea, (N,N'-bis-(1,1-dimethyl-2-propynyl)urea), is especially preferred.

SYNTHESIS OF THE COMPOUNDS

The symmetrical alkynyl ureas of the general formula can be made by reacting an amino-alkyne having an alkynyl group of from 3 to 5 carbon atoms with a beta-chloroethylchloroformate or a beta-fluoroethylchloroformate in a mixture of water, diethylether, and triethylamine at a temperature within the range of 24° to 32° C., at a mole ratio of from 0.5 to 1.5 of amino-alkyne to chloroformate, and then separating the symmetrical alkynyl urea from the mixture.

These reaction conditions are substantially those usually used for making a carbamate by the reaction of a chloroformate and an amine.

The preferred symmetrical alkynyl ureas are made by reacting the amino-alkynyls of 3-amino-1-propynyl, 1-amino-2-butyne, 4-amino-1-butyne, 1-amino-2-pentyne, 5-amino-2-pentyne, 5-amino-1-pentyne, or 3-amino-3-methyl-1-butyne with either a beta-chloroethylchloroformate or beta-fluoroethylchloroformate under reaction conditions mentioned above. Beta-fluoroethylchloroformate is the preferred chloroformate to use in this invention.

The following example illustrates the way of making these symmetrical alkynyl ureas, by the reaction of an amino-alkyne and a chloroformate under conditions substantially used to make carbamates.

EXAMPLE I

Synthesis of bis-(3-methyl-1-butyn-3-yl)urea also called bis-(1,1-dimethyl-2-propynyl)urea The structural formula of this urea is

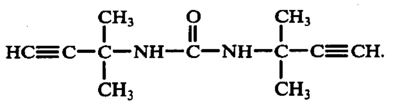

The amino-alkyne of 3-amino-3-methyl-1-butyne (5.0 grams, 0.06 mole) was added to a solution of triethylamine (6.1 grams, 0.06 mole) in water (100 milliliters) contained in a 500 milliliter 3-necked creased (Morton) flask, which was equipped with a mechanical stirrer, thermometer, water-cooled condenser and a pressure-equalizing dropping funnel. Diethylether (100 milliliters) was added and vigorous stirring begun. The chloroformate of 2-fluoroethyl chloroformate (7.6 grams, 0.06 mole) was added dropwise over an 8-minute period, during which time the temperature rose from 24° to 32° C., and a gentle reflux of ether was noted. After the addition was completed, the reaction mixture was stirred at ambient temperature for an additional hour. The layers were separated and the aqueous layer was washed with 100 milliliters of diethylether. The combined organic layers were washed successively with 100 milliliters of 10 percent aqueous sodium hydroxide, 10 percent aqueous hydrochloric acid, and water, and the washed organic layers were dried over anhydrous sodium sulfate. The drying agent was filtered off and the solvent removed on a rotary evaporator to give 4.2 grams of mushy white crystals, which were recrystallized from benzene-hexane. White needles (1.8 grams, 30 percent yield based on starting amine), melting at 184°–186.5° C., were filtered off. The infrared spectrum showed absorption at 3340 and 3290 $cm^{-1}$ (NH) and 1640 $cm^{-1}$ (carbonyl). Nuclear magnetic resonance (NMR) spectroscopy showed that there was no fluoroethyl group present, and that there was a simple spectrum with singlets at (downfield from TMS)δ 5.60 (N-H), 2.37 (—C≡C—H) and 1.60 ($—CH_3$) in a ratio of 1:1:6. The above spectroscopic data indicated that the product was N,N'-bis-(3-methyl-1-butyn-3-yl)urea. This was confirmed by combustion elemental analysis.

Calculated for: $C_{11}H_{16}N_2O$: C, 68.71; H, 8.39; N, 14.57.

Found: C, 67.79, 67.88; H, 8.13, 8.21; N, 14.26, 14.44.

The filtrate from above was evaporated to give 2.4 grams (23.1 percent yield based on chloroformate) of colorless liquid, which had an infrared absorption at 3300 $cm^{-1}$ (NH) and 1710 $cm^{-1}$ (carbonyl). The NMR spectrum was consistent with the structure, beta-fluoroethyl N-3-methyl-1-butyn-3-yl carbamate.

Alternatively, the symmetrical alkynyl ureas may be synthesized by the reaction of the amino-alkynes with phosgene. For example, N,N'-bis-(3-methyl-1-butyn-3-yl)urea may be synthesized by the reaction of 3-amino-3-methyl-1-butyne with phosgene according to the following procedure:

To a 500 milliliter benzene solution containing 0.10 mole of 3-amino-3-methyl-1-butyne, at 0° to 80° C., 0.20 mole of phosgene is bubbled into the agitated solution, and the solution is stirred for 2–4 hours. The reaction mixture is mixed with water (500 milliliters) and the organic layer and water layer are separated. The organic layer is washed first with 100 milliliters of 10 percent hydrochloric, with 100 milliliters of 10 percent aqueous solution of sodium hydroxide, and then with 100 milliliters of distilled water, and then the washed organic layer is dried over sodium sulfate, and filtered. Benzene is removed by evaporation to form the crystalline material of bis-(3-methyl-1-butyn-3-yl)urea.

PROPERTIES OF THE SYMMETRICAL ALKYNYL UREAS

The properties of these symmetrical alkynyl ureas are shown by the following tests using N,N'-bis-(3-methyl-1-butyn-3-yl)urea.

Control of the Weeds of the Genus Cyperus

The use of the symmetrical alkynyl ureas as a herbicide may be shown in various ways. For example, in laboratory testing, it is common to mix a compound with acetone, alone or with methanol and/or dimethyl formamide, to form a solution that may later be emulsified with water and then sprayed onto soil in which seeds have recently been planted or in which young plants are growing but have not emerged, which application is referred to as a pre-emergence application. In testing of this kind, N,N'-bis-(3-methyl-1-butyn-3-yl)urea exhibited the ability to control the growth of yellow nutsedge tubers grown under natural sunlight when applied at a rate of 10 pounds per acre per 6 inch depth of soil in the pre-emergent mode.

In this testing, the compound was applied as an aqueous emulsion produced from a concentrate based upon 90 weight percent acetone, 8 weight percent methanol and 2 weight percent dimethyl formamide. Similar testing of various grasses indicates a selective herbicidal action; the novel urea is tolerated by grassy plants, of the genus Mays, such as corn, when applied at rates that are herbicidal to yellow nutsedge.

Control of Fungi of the Genus Sclerotium

N,N'-bis-(3-methyl-1-butyn-3-yl)urea controls the deleterious effect of soil fungi of the genus Sclerotium when fungi or a fungus is contacted with an amount effective to control the deleterious effect of the fungi. For example, the deleterious effect of the particular fungus *Sclerotium rolfsii*, a cause of Stem Rot of Peanuts, is controlled when the fungus is contacted with the compound as shown by the following laboratory test.

Sterile soil having 8 grams of the sclerotia of *Sclerotium rolfsii* per 3000 milliliters of dry soil, was chemically treated by mixing it with N,N'-bis-(3-methyl-1-butyn-3-yl)urea at a rate of 50 pounds per acre per 6 inch depth of soil. The treated soil was placed in a container, implanted with two carrot slices, water sealed, and the container was placed for 4 to 5 days of observation in a glass covered greenhouse operating at a temperature of 70° to 80° F. and a humidity of 50 to 90 percent. The final observation was made on the fifth day. Containers with sterile soil and *Sclerotium rolfsii* only, and sterile soil and the chemical were also implanted with carrot slices and observed. Three replicates were used.

Control effectiveness was determined by comparing the actual count of infection loci on carrot slices in soil having both the fungus and the chemical (treated carrots), with that found in soil having only the fungus (control carrots). This control effectiveness is expressed as percent control by the following formula:

Percent Control =

$$100\% - \frac{\text{(number of infection loci in all treated carrots)}}{\text{(number of infection loci in all control carrots)}} \times 100\%$$

Under these tests the compound at 50 pounds per acre per 6 inch depth of soil gave a 66 percent control.

Control of the Fungi Phytophthora

N,N'-bis-(3-methyl-1-butyn-3-yl)urea effectively controls the deleterious effects of the fungi of the genera Phytophthora when an effective amount of the urea contacts the fungi, especially the fungus *Phytophthora infestans,* which causes Late Blight of Tomatoes, particularly when the compound is applied to the plants as a protectant against the deleterious effects of the fungus *Phytophthora infestans* as shown by the following laboratory test.

Bonny Best tomatoes grown under natural sunlight until they are five to six weeks old and in the five leaf growth stage, were mounted on a compound turntable and sprayed to incipient run off at 40 pounds pressure for 60 seconds, which is equivalent to a spray rate of 50 gallons per acre. The test solution spray contained 1000 parts per million (ppm) of the urea, and was formed by diluting a stock emulsion solution containing 1995 milliliters of acetone, 4 milliliters of SPAN 85® (sorbitan trioleate) and 1 milliliter of TWEEN 80® (sorbitan monooleate polyalkylene derivative).

After the chemically treated plants had dried (4–8 hours), they were inoculated by uniformly spraying them with a mixed sporangial and zoaspore suspension of the fungus *Phytophthora infestans,* taken directly from diseased plants, $10^6$ zoaspores and $10^5$ sporangia per 35 plants per replicate. Three replicates were used. Then the plants were incubated in the dark at 70° C. (21° Centigrade) and 95 percent or more relative humidity, for 40 hours which normally insures that the spores infected the plants, and then the plants are placed in a glass greenhouse using natural sunlight, at a temperature of 21°–33° Centigrade and 50 to 90 percent humidity, and observed for signs visible to the naked eye of total infection lesions of top three leaves (generally 3–5 days to develop).

The control effectiveness was determined by comparing the actual count of developed lesions on chemically treated plants and those on chemically untreated, but inoculated plants (control plants), and was calculated as follows:

Percent Control =

$$100\% - \frac{\text{(number of lesions per treated plants)}}{\text{(number of lesions per control plants)}} \times 100\%$$

Under these test conditions the urea compound at 1000 parts per million gave 27 percent control.

Control of the Bacterium of the Genus Xanthomonas

The symmetrical urea effectively controls the deleterious effects of bacterium of the genus Xanthomonas when an effective amount of the urea contacts one of these bacterium, especially when the urea is applied to the foliage of the plant prior to the plant contacting the bacterium, particularly *Xanthomonas vesicatoria* which causes bacterial Leaf Spot of Tomatoes. This is shown by the following laboratory test.

Tomato plants were grown and sprayed as described herein for the test for the protectant control of *Phytophthora infestans,* and dried. They were then inoculated by uniformly spraying at a rate of 200 milliliters per 70 plants, with a solution containing from 90,000 to 120,000 spores of 60 days old bacteria of *Xanthomonas vesicatoria* and 5 grams of carborundum. After an incubation in the dark for 40 hours at 80° F. (255° C.) and 95 percent humidity, a time sufficient to insure infestation by the bacteria; the plants were placed in a greenhouse, which used natural sunlight and operated at 70° to 80° F. and 50 to 95 percent humidity to allow lesions to develop. The lesions generally developed after 9 days to the stage where they are visible to the naked eye.

The percent control was determined by comparing the actual count of the lesions developed on the chemically treated and inoculated plants (treated plants) with those developed on inoculated plants (control plants). The percent control was calculated as follows:

Percent Control =

$$100\% - 100\% \frac{\text{(number of lesions on treated plants)}}{\text{(number of lesions on control plants)}}$$

The percent control obtained with 1000 parts per million of N,N'-bis-(3-methyl-1-butyn-3-yl)urea under these conditions was 32 percent.

APPLICATION AND METHOD OF CONTROL OF PLANT PESTS

Weeds of the genus Cyperus and particularly those of *Cyperus esculentus* (Yellow nutsedge) are controlled by contacting the weed with one or more of the symmetrical alkynyl ureas in an amount effective to control the weeds. As used herein and in the claims the phrase "in an amount effective to control the weeds" is from 5 to 50 pounds per acre per 6 inch depth of soil, normally it is from 6 to 25 pounds per acre, and generally it is from 10 to 15 pounds per acre, applied pre-emergence to the weeds, that is prior to the emergence of true leaves.

The pre-emergence application is made in any manner whatsoever, for example by spraying the soil with a solution of the active compound, by dusting the soil with the compound, or by broadcasting it on the ground and discing the dust into the ground. The important point is that the weed emerging from the tuber, or the tuber itself is contacted with the active compound before the young plant grows hardy. Of course several applications of one or more of the ureas may be made, or may be combined with other herbicides, pesticides, or fungicides. Thus for crop plants such as corn (*Zea mays*) the urea can be applied with fertilizer prior to emergence of weeds of the genus Cyperus, particularly the species *Cyperus esculentus,* so as to control them.

Those symmetrical alkynyl ureas of the general formula in which R is an alkynyl of 2-propynyl, 2-butynyl, 3-butynyl, 2-pentynyl, 3-pentynyl, 4-pentynyl, 1-methyl-2-propynyl, 1-ethyl-2-propynyl, and 1,1-dimethyl-2-propynyl are preferred for controlling these weeds. Those symmetrical alkynyl ureas in which R is 2-propynyl, 1-methyl-2-propynyl, and 1,1-dimethyl-2-propynyl are highly preferred for control of these weeds.

Especially preferred is N,N'-bis-(3-methyl-1-butyn-3-yl)urea for controlling these weeds, especially the weed Yellow nutsedge (*Cyperus esculentus*) which are not mutant strains resistant to ureas. This particular urea is normally applied at the rate of 5 to 15 pounds per acre per .6 inch depth of soil prior to emergence of the weed.

As used herein and in the claims the phrase "to control the weeds" means to impede the growth of the weeds; this can be by killing them or stunting from 10 to 100 percent of the weeds to the point where natural or cultivated plants choke the weeds out.

Those symmetrical alkynyl ureas of the general formula in which R is 2-propynyl, 1-methyl-2-propynyl, and 1,1-dimethyl-2-propynyl, are normally used to control the deleterious effects of a bacterium of the genus Xanthomonas, or a fungus of the genus Phytophthora upon a plant, by contacting the bacterium or fungus with the urea in an amount effective to control the deleterious effects of bacterium or fungus upon the plant. N,N'-bis-(3-methyl-1-butyn-3-yl)urea is especially preferred.

The phrase "an amount effective to control the deleterious effect of the fungus" or, "an amount effective to control the deleterious effect of the bacterium" as used herein and in the claims refers to from 100 to 20,000 parts per million (ppm) of a urea applied to the plant at a rate of from 30 to 60 gallons per acre to incipient run off. Generally it is from 400 to 10,000 ppm, but normally it is from 1000 to 5000 ppm.

The term "contact" refers to any method of applying urea, such as N,N'-bis-(3-methyl-1-butyn-3-yl)urea to the plant, so that the fungus or bacterium and compound contact each other. Preferably, however, the application is prior to when the plant shows signs of the deleterious effects of the bacterium or fungus, e.g., after planting the plants, or when they emerge from the soil and have true leaves. The application can be by spraying or by dusting, and this can be done with one or more other known fungicides, bactericides, or pesticides. Of course one or several applications of an urea may be made during the growing season to maintain this control on plants affected by the bacteria of the genus Xanthomonas and/or fungi of the genus Phytophthora, particularly by the species *Xanthomonas vesicatoria* and *Phytophthora infestans.*

The symmetrical alkynyl ureas in which R is 2-propynyl, 2-butynyl, 3-butynyl, 2-pentynyl, 3-pentynyl, 4-pentynyl, 1-methyl-2-propynyl, 1-ethyl-2-propynyl, and 1,1-dimethyl-2-propynyl are used to control the deleterious effect of a fungus of the genus Sclerotium by contacting the fungus with one or more of the above mentioned ureas in an amount effective to control the deleterious effect of the fungus upon the plant.

Preferably the symmetrical alkynyl urea in which R is 2-propynyl, 1-methyl-2-propynyl, and 1,1-dimethyl-2-propynyl are used to control the deleterious effects of a fungus of the genus Sclerotium upon a plant. The urea N,N'-bis-(3-methyl-1-butyn-3-yl)urea is especially preferred. The fungus species *Sclerotium rolfsii* is especially controlled by the use of these ureas, particularly by N,N'-bis-(3-methyl-1-butyn-3-yl)urea.

The phrase "an amount effective to control the deleterious effects of the fungus of Sclerotium" as used herein and in the claims refers to from 10 to 150 pounds of the urea applied per acre per 6 inch depth of soil, but generally it is from 15 to 100 pounds, and normally from 30 to 60 pounds, applied to the soil. The application is prior to the planting of crops, and one or more applications may be made, together with fertilizer or other pesticides to control the effects of the fungi. The compound may be applied as a solution or as a dust and then disced into the soil, or allowed to seep into the soil in the presence of water, e.g., by irrigation.

The phrase "control of the deleterious effect of the fungus" or "control of the deleterious effect of the bacterium" as used herein and in the claims means to reduce the deleterious effect of the fungus or bacterium on the plant; that is that from 10 to 100 percent of the plants treated with the urea is free of the disease caused by these fungi or bacteria in comparison to plants which are not treated by the chemical.

While the invention has been described with reference to specific details of certain illustrative embodiments, it is not intended that it shall be limited thereby except insofar as such details appear in the accompanying claims.

I claim:

1. A method of controlling a weed of the genus Cyperus which comprises contacting the weed with a composition in an amount effective to control the weed, the composition having the general formula:

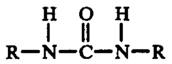

wherein: R is an alkynyl of from three to five carbon atoms.

2. The method of claim 1, wherein R is an alkynyl selected from the group consisting of 2-propynyl, 2-butynyl, 3-butynyl, 2-pentynyl, 3-pentynyl, 4-pentynyl, 1-methyl-2-propynyl, 1-ethyl-2-propynyl, and 1,1-dimethyl-2-propynyl.

3. The method of claim 1, wherein R is an alkynyl selected from the group consisting of 2-propynyl, 1-methyl-2-propynyl, and 1,1-dimethyl-2-propynyl.

4. A method of controlling a weed of the genus Cyperus which comprises contacting the weed with N,N'-bis-(3-methyl-1-butyn-3-yl)urea in an amount effective to control the weed.

5. The method of claim 4, wherein the weed is Yellow nutsedge (*Cyperus esculentus*).

6. The method of claim 4, wherein the weed is growing in an environment comprising crop plants of the genus Zea and said urea is applied to said environment at a rate of from 5 to 15 pounds per acre per 6 inch depth of soil prior to emergence of said weed.

7. The method of claim 4, wherein the crop plant is corn (*Zea mays* (L.)) and said weed is Yellow nutsedge (*Cyperus esculentus*).

* * * * *